United States Patent
Aose et al.

[11] Patent Number: 5,838,843
[45] Date of Patent: Nov. 17, 1998

[54] MULTIPURPOSE OPTICAL SENSOR

[75] Inventors: Shinichi Aose; Koichi Miura; Takashi Hiyama, all of Tokai-mura, Japan

[73] Assignee: Doryokuro Kakunenryo Kaihatsu Jigyodan, Tokyo, Japan

[21] Appl. No.: 604,742

[22] Filed: Feb. 23, 1996

[30] Foreign Application Priority Data

Mar. 6, 1995 [JP] Japan .................................. 7-045462

[51] Int. Cl.$^6$ ............................................. G02B 6/04
[52] U.S. Cl. ................................ 385/12; 385/13; 356/73.1
[58] Field of Search ............................. 385/12, 13, 126, 385/115, 116; 250/575; 356/73.1

[56] References Cited

U.S. PATENT DOCUMENTS

| | | |
|---|---|---|
| 4,534,651 | 8/1985 | Minikane . |
| 4,561,779 | 12/1985 | Nagamune et al. . |
| 4,648,082 | 3/1987 | Savit ................................ 385/12 |
| 4,848,871 | 7/1989 | Seidel et al. . |
| 5,371,600 | 12/1994 | Hsia et al. . |
| 5,552,604 | 9/1996 | Sting et al. ..................... 250/341.2 |

FOREIGN PATENT DOCUMENTS 1189840  4/1970  United Kingdom .

WO 88/0210  3/1988  WIPO .

*Primary Examiner*—John D. Lee
*Assistant Examiner*—Ellen Eunjoo Kang
*Attorney, Agent, or Firm*—Armstrong, Westerman, Hattori, McLeland, & Naughton

[57] ABSTRACT

A multipurpose optical sensor including an even number of optical fiber bundles, and optical systems for converting light guided through optical fiber bundles and leaving leading ends of optical fiber bundles into a substantially parallel light beam in a direction at right angles with the axes thereof, and converging substantially parallel light beam incident on axes from a direction at right angles therewith and guiding the thus converged light beam from leading ends into optical fiber bundles in the form of guide light. The optical fiber bundles are concentrically located in the vicinity of leading ends and, one set of optical systems for a pair of opposing optical fiber bundles, with the center of the concentric circle being positioned therebetween, is opposed to each other at an interval and disposed such that substantially parallel light beam leaving one set of optical systems is incident on other set of optical systems, and trailing ends of the even number of optical fiber bundles are constructed such that trailing ends separately receive or give out light.

15 Claims, 5 Drawing Sheets

MULTIPURPOSE OPTICAL SENSOR

BACKGROUND OF THE INVENTION

The present invention relates to a multipurpose optical sensor, and more particularly to a multipurpose optical sensor designed to separately or simultaneously effect analyses such as absorptiometric analysis, fluorescent analysis, and scattering analysis at identical or different positions of fluids such as liquids, and gases. The present invention is also concerned with a multipurpose optical sensor best-suited for analyses such as absorptiometric analysis, fluorescent analysis, and scattering analysis in radiation environments, e.g., in atomic power fields.

So far, a single optical sensor has generally been used for one purpose, e.g., for absorptiometric analysis. For instance, a optical sensor is used for absorptiometric analysis to detect light absorption spectra. Never until now, however, is there known a technique enabling a single optical sensor to be used for multiple purposes, for instance, to simultaneously detect light absorption spectra, fluorescence spectra, etc., while the influence rate of radiation is measured concurrently with control of quantity of light, and to simultaneously detect a plurality of light spectra at a plurality of measuring points.

It is therefore an object of the present invention is to provide a multipurpose optical sensor which enables optical fibers to be used to separately or simultaneously effect analyses such as absorptiometric analysis, fluorescent analysis, and scattering analysis at identical or different positions of fluids such as liquids, and gases.

SUMMARY OF THE INVENTION

According to the present invention, there is provided a multipurpose optical sensor including an even number of optical fibers or optical fiber bundles, and optical systems for converting light guided through said optical fibers or optical fiber bundles and leaving leading ends of said optical fibers or optical fiber bundles into a substantially parallel light beam in a direction at right angles with the axes thereof, and converging said substantially parallel light beam incident on said axes from a direction at right angles therewith and guiding the thus converged light beam from said leading ends into said optical fibers or optical fiber bundles in the form of guide light, said optical fibers or optical fiber bundles being concentrically located in the vicinity of said leading ends, one set of said optical systems for a pair of opposing optical fibers or optical fiber bundles, with the center of the concentric circle being positioned therebetween, being opposed to each other at an interval and disposed such that said substantially parallel light beam leaving said one set of said optical systems is incident on other set of said optical systems, and trailing ends of the even number of said optical fibers or optical fiber bundles being constructed such that said trailing ends separately receive or give out light.

In one preferable embodiment, the optical systems are each constructed from a positive lens and a reflecting mirror or prism.

Alternatively, the optical systems are each constructed from a 90°-bent leading end portion of the optical fiber or optical fiber bundle and a positive lens.

In another preferable embodiment, when the pairs of opposing optical fibers or optical fiber bundles are each deemed as one set, the optical systems located at the leading ends of different sets lie on axially identical positions.

Alternatively, when the pairs of opposing optical fibers or optical fiber bundles are each deemed as one set, axial positions of the optical systems located at the leading ends of different sets are different regarding at least one set.

In still another preferable embodiment, the leading ends of the even number of optical fibers or optical fiber bundles are positioned at regular intervals on said concentric circle.

According to the present invention, by selecting as equipment connected to the trailing ends of the even number of optical fibers or optical fiber bundles any of a light source, an excitation light source, a spectrometric analyzer, an actinometer, and the like, it is possible to use a single optical sensor to simultaneously effect the desired measurements for many purposes, e.g., absorptiometric, fluorophotometric, actinometric, and scattering-measuring purposes. It is also possible to use a single optical sensor to effect a plurality of measurements of a plurality of samples while the influence index of radiation is corrected.

DETAILED EXPLANATION OF THE PREFERRED EMBODIMENTS

The principles and embodiments of the multipurpose optical sensor according to the present invention will now be explained with reference to the drawings.

Figure 1:
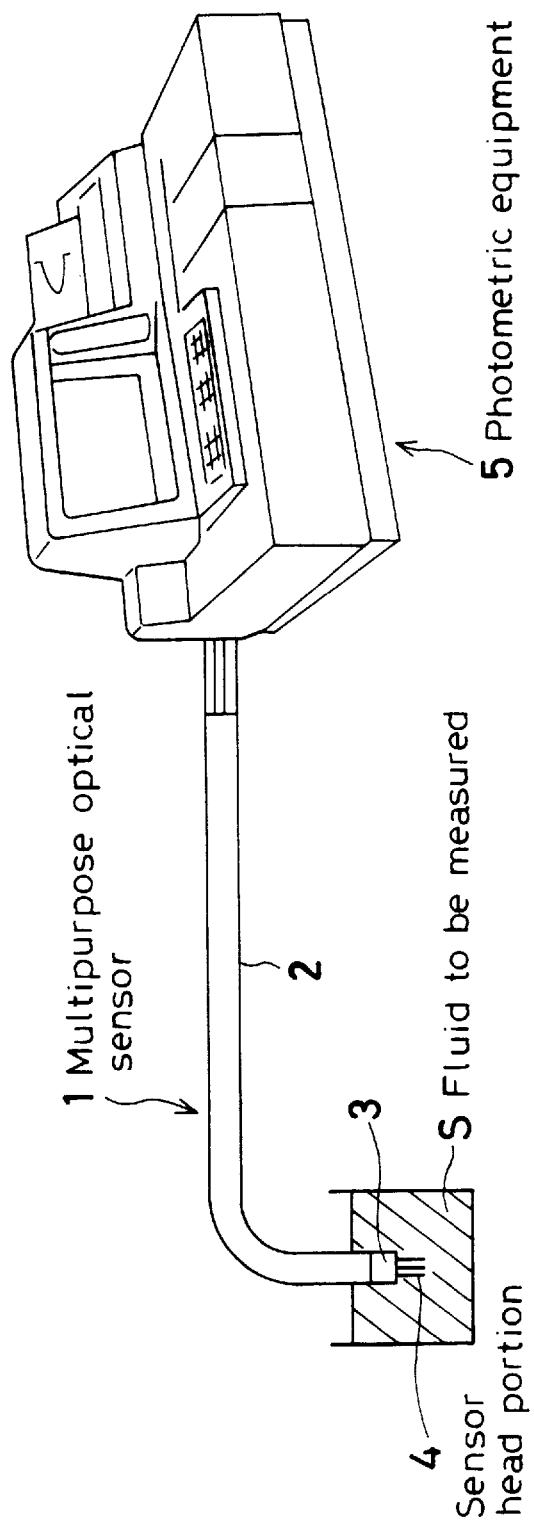
FIG. 1 is a schematic illustrating a general arrangement of the multipurpose optical sensor according to the first embodiment of the invention, which is constructed in the form of photometric equipment.
Figure 2:
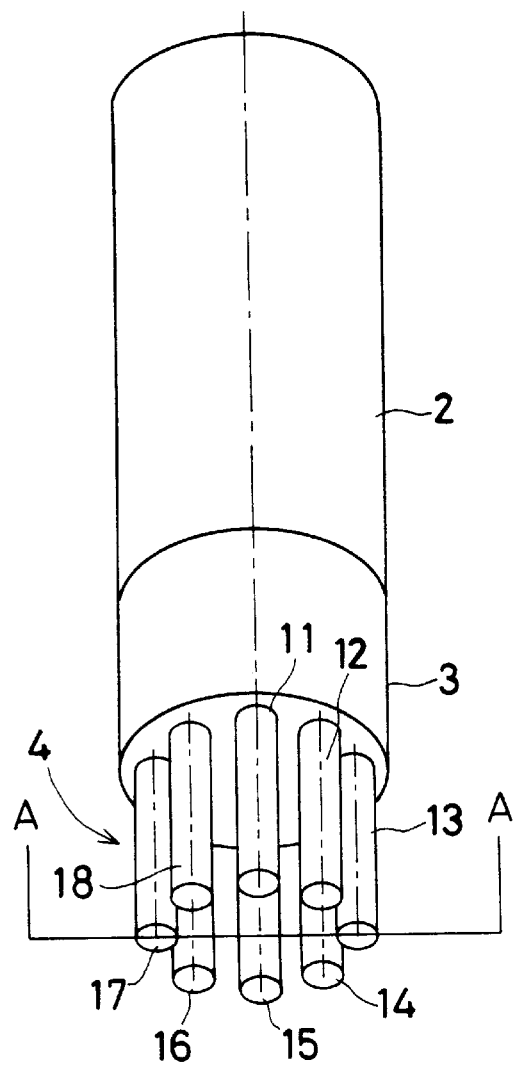
FIG. 2 is an enlarged perspective view of leading ends of the multipurpose optical sensor according to the first embodiment.
Figure 3:
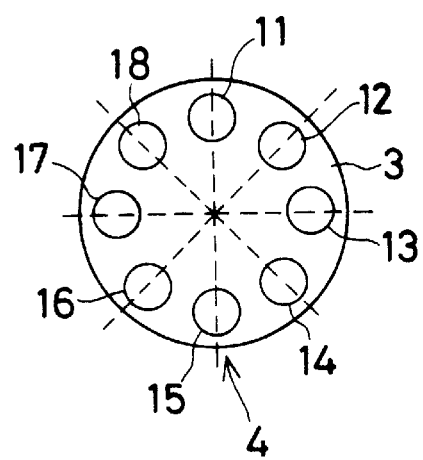
FIG. 3 is a schematic, as viewed from below, of the leading ends of the multipurpose optical sensor according to the first embodiment.

FIG. 1 shows a general arrangement of a first embodiment of the multipurpose optical sensor according to the present invention, which is here constructed in the form of measuring equipment, and FIG. 2 is an enlarged perspective view of leading ends thereof while FIG. 3 is a schematic of those ends as viewed from below. A multipurpose optical sensor, shown generally at 1, includes a flexible cable member 2 in which at least two pairs (for pairs in the embodiment described herein) of optical fiber bundles are enclosed and bound together with the exception of their leading ends. The leading ends 11 to 18 of the optical fiber bundles project concentrically from a leading end 3 of the cable member 2 and extend from positions, where a pair of leading ends are diametrically opposite to each other with the center of the concentric circle being located therebetween, by the same length in a direction parallel with the axial direction of the cable member 2. The extending portions of the leading ends 11 to 18 and the leading end 3 are hard enough to be not bent even upon the application of external force or the like thereto. Thus, the leading ends 11 to 18 as a whole constitute a sensor head portion 4. In use, it is this sensor head portion 4 that is directly immersed in the fluid S to be measured for absorptiometric or other analysis purposes.

As will be described later, the trailing ends of the optical fiber bundles at the trailing end of the cable member 2 are designed to be connectable to a light source, a spectrometric portion and an actinometric portion of photometric equipment 5 such as an absorptiometer, a fluorophotometer, and an actinomer, although depending on measuring purposes. No detailed account of the structure for connecting the trailing ends of the optical fiber bundles to the light source or measuring portions is here given because any of known structures may be used for this purpose.

Figure 4:
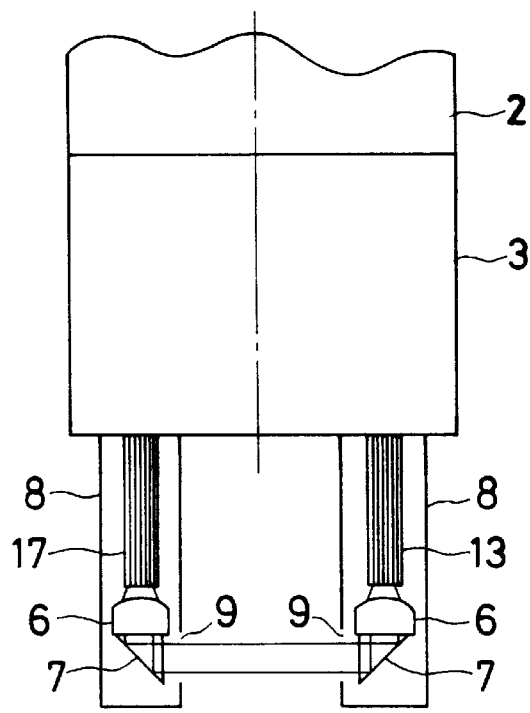
FIG. 4 is a sectional view taken along the line A-A' in FIG. 2.

FIG. 4 is a sectional view taken along the line A-A' in FIG. 2, including the center of the concentric circle wherein the leading ends 11 to 18 are arranged. This view is a sectional view regarding a pair of leading ends 13 and 17, and is also true of the remaining pairs of leading ends 11 and 15, 12 and 16, and 14 and 18. The pair of leading ends 13 and 17 extending concentrically from the leading end 3 of the cable member 2 is put in cases 8 and 8 having windows 9 and 9 in positions where they are opposite to each other with the center of the concentric circle located therebetween, so that they can be protected against external force. In the cases 8, there are located positive lenses 6 in front of the leading ends 13 and 17 of the optical fiber bundles, which enable light beams emanating from the optical fiber bundles to be converted into substantially parallel light, and light beams propagating toward the leading ends of the optical fiber bundles to be converged into guide light for the optical fiber bundles. In front of the positive lenses 6 there are located reflecting prisms 7 of quartz, which enable the light emanating from the leading ends of the optical fiber bundles and made parallel to be converted into light that propagates at right angles with the axis of the optical fiber bundle and toward the center of the above-mentioned concentric circle, and the light emanating from the center of the above-mentioned concentric circle and striking on the axis of the optical fiber bundle to be turned in the axial direction thereof. In addition, the reflecting prisms 7 for the leading ends 11 to 18 are all located at the same height positions.

Thus, the light beam propagating through one of the pair of optical fiber bundles with the center of the concentric circle located between them leaves its leading end, e.g., 13, and is made a parallel beam through the positive lens 6, which is in turn bent 90° through the reflecting prism 7. The thus bent light beam then enters the window 9, passes through the fluid S to be measured, which is penetrating between the windows 9 and 9, enters the window 9 for the leading end of the opposite fiber bundle, 17 in this case, and is bent 90° through the reflecting prism 7 along the axial direction of the optical fiber bundle, is converged into the leading end of the optical fiber bundle through the positive lens 6, and is finally bound together through the optical fiber bundle in the form of guide light.

Figure 5:
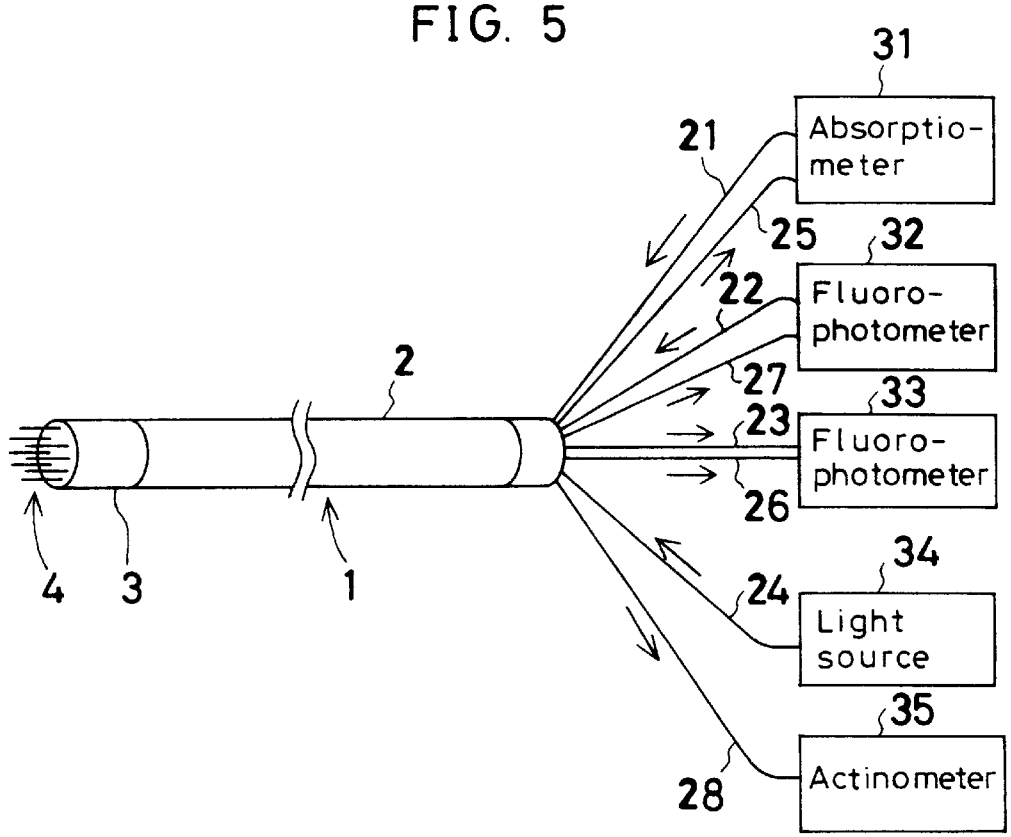
FIG. 5 is a schematic presented for illustrating the connection of the multipurpose optical sensor according to the invention to photometric equipment such as an absorptiometer.

According to such construction as shown in FIG. 5 wherein light source and spectrometric portions of an absorptiometer 31, for instance, are connected to any of the pairs of trailing ends 21 and 25, 22 and 26, 23 and 27, and 24 and 28 of the optical fiber bundles terminating at the pairs of opposite leading ends 11 and 15, 12 and 16, 13 and 17, and 14 and 18, it is possible to find light absorption spectra of the fluid S to be measured. By connecting excitation light source and photometric portions of fluorophotometers 32 and 33 to unpaired trailing ends of the optical fiber bundles, for instance, 22 and 27, and 23 and 26, it is also possible to find fluorescence, scattering and other spectra of the fluid S to be measured. Furthermore, by connecting a light source 34 and an actinometer 35 to the trailing ends 24 and 28 of the optical fiber bundles terminating at a pair of opposite leading ends, e.g., 14 and 18, it is possible to find the absorbency index of the fluid S to be measured. In addition, since at least two pairs of opposite leading ends 11 to 18 (four pairs in this embodiment) are provided, it is possible to effect these measurements at the same time. Some illustrative examples of these measurements will be given below.

EXAMPLE 1

Absorptiometric Measurement

Referring to FIGS. 2 and 3, the leading ends 11, 12, 13 and 14 are connected to a light source on the light-projecting side while the leading ends 15, 16, 17 and 18 are connected to a spectrometric portion. That is, (four) pairs of leading ends 11 and 15, 12 and 16, 13 and 17, and 14 and 18 can be used for the simultaneous measurement of light absorption spectra in four directions. It is here to be noted that if the light-receiving ends of the four pairs of leading ends are combined into a single unit for connection to a single spectrometric portion, it is then possible to effect analysis at large quantities of light. In the example described above, the positive lenses 6 and reflecting prisms 7 are provided for all the leading ends 11 to 18 on the light-projecting and -receiving sides, so that light-collecting and -receiving powers can be increased to obtain large quantities of light as a whole. However, it is to be noted that when the light of quantity is too large, it can be controlled by the provision of three or two pairs of leading ends rather than the four pairs of leading ends. When the fluid S flowing through piping is measured, the fluid S flows between the respective leading ends 11 to 18 of the sensor head portion 4. If the leading ends 11 to 18 are positioned at circumferentially regular intervals, however, there is then merit in that the same flow rate can constantly be obtained, because the resistance thereof to flow has no dependence on an angular direction when inserted through piping.

EXAMPLE 2

Fluorophotometry

Referring to FIGS. 2 and 3, the leading end 11 is connected to an excitation light source so as to receive fluorescence at the leading ends 12, 13, 14, 15, 16, 17 and 18, which are connected to a spectrometric portion separately or in the form of a single unit so that fluorescence spectra can be measured. It is to be noted that if the leading ends 12, 13, 14, 15, 16, 17 and 18 are separately connected to the spectrometric portion, it is then possible to measure the dependence of fluorescence spectra on angles. When the quantity of excitation light is small, it can be controlled by connecting the leading end 11 plus the leading end 12 to the excitation light source so as to receive light at the leading ends 13, 14, 15, 16, 17 and 18.

EXAMPLE 3

Simultaneous Asorptiometric and Fluorophotometric Measurements

Referring to FIGS. 2 and 3, if the leading ends 11 and 15 are connected to a light source and a spectrometric section, respectively, it is then possible to effect absorptiometry, and if the leading ends 12, 13, 14, 16, 17 and 18 are connected to another spectrometric portion, it is then possible to effect fluorophotometry at the same time. As is the case with (Example 1) and (Example 2), the quantity of light can be controlled.

Figure 6:
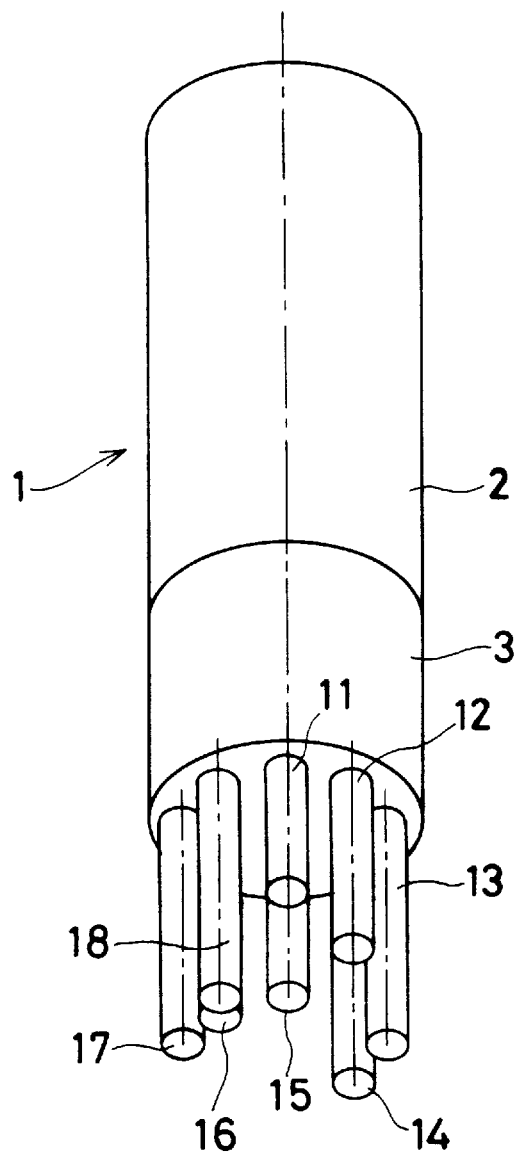
FIG. 6 is an enlarged perspective view of leading ends of the multipurpose optical sensor according to the second embodiment.

Reference is then made to a second embodiment of the present invention. As shown in FIG. 6, pairs or sets of opposing leading ends 11 and 15, 12 and 16, 13 and 17, and 14 and 18 are varied in terms of axial length. In the embodiment shown in FIG. 6, the set of leading ends 11 and 15 have the shortest length, the set of leading ends 12 and 16 have an intermediate length, and the sets of leading ends 13 and 17, and 14 and 18 have the longest length. A multi-purpose optical sensor 1 having the leading ends varying in length enables multiple flow passages to be simultaneously measured in terms of the intensity of absorbed light, etc. This also allows measurements to be effected in radiation environments while a pair of leading ends having a varying length is used as a criterion for correction.

EXAMPLE 4

Simultaneous Measurement of Multiple Flow Passages

Figure 7:
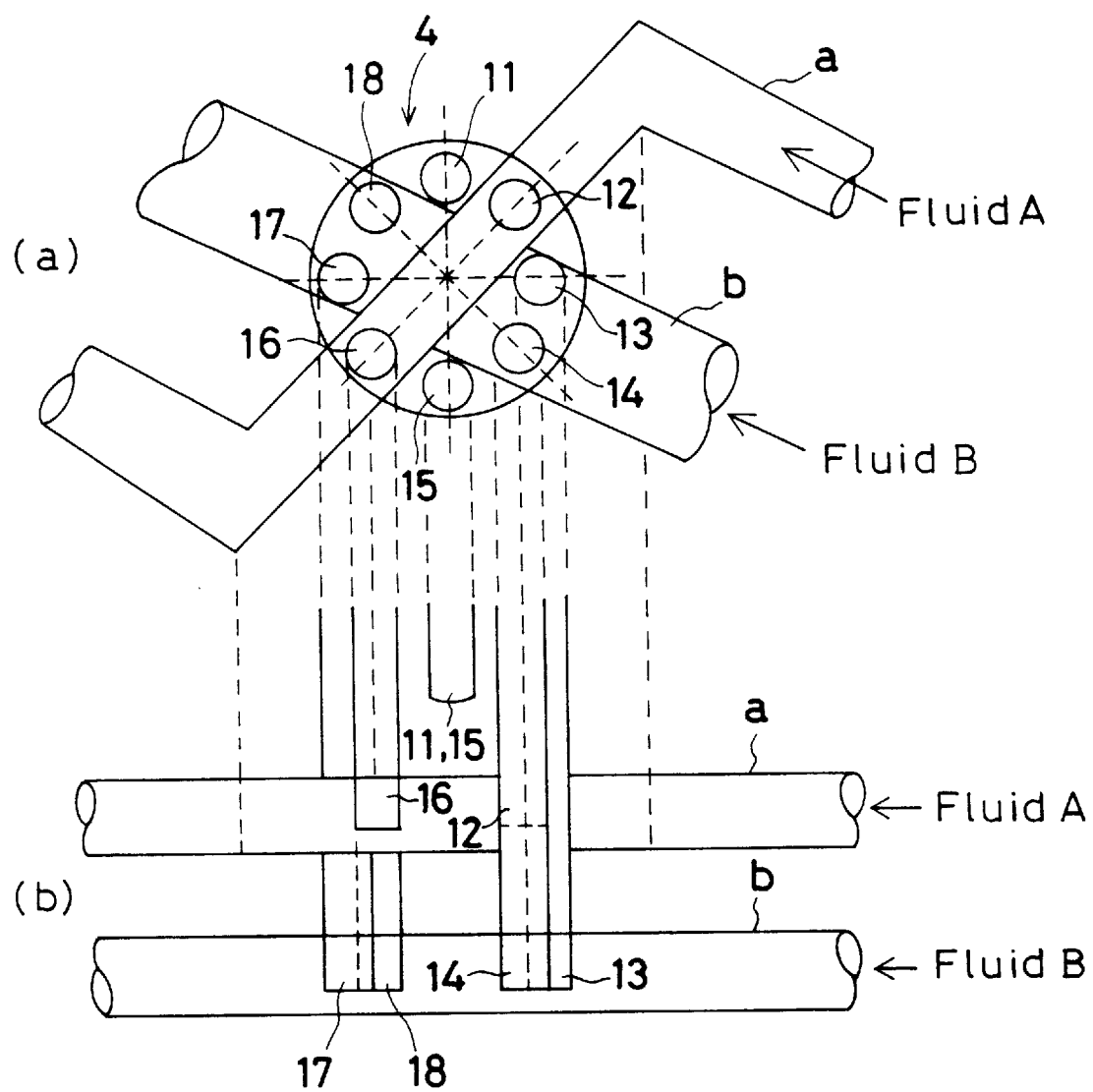
FIG. 7 is schematics, as viewed from above and sideways, of an arrangement for measuring multiple flow passages at the same time, using the multipurpose optical sensor according to the second embodiment.

FIG. 7 illustrates an arrangement for the simultaneous absorptiometric and other measurements of fluids A and B flowing through two pipes a and b at their intersecting point, with (a) and (b) being schematics as viewed from above and sideways, respectively. In the arrangement, the multipurpose optical sensor 1 according to the above-mentioned second embodiment is used while a pair of leading ends 12 and 16 is inserted through the pipe a and pairs of leading ends 13 and 17, and 14 and 18 are inserted through the pipe b. A pair of leading ends 11 and 15 is located in the air without being immersed in the fluids. Absorptiometric measurement of fluid A can be made by locating the leading end 12 on the light-projecting side and the leading end 16 on the light-receiving side while absorptiometric measurement of fluid B can be carried out by locating 13 on the light-projecting side and 17 on the light-receiving side. Fluorophotometric measurement of the fluids can be practiced by locating 14 and 18 on the fluorescence-receiving side. Thus, absorptiometric and fluorophotometric measurements can be effected at the same time.

EXAMPLE 5

Measurement in Radiation Environments

In radiation environments, optical fibers degrade due to radiation, resulting in a decrease in the transmittance of light. Thus, absorptiometric and other measurements must be effected while this rate of decrease is constantly compensated for. In an arrangement shown in FIG. 7, a pair of leading ends 11 and 15, which is not immersed in the fluids A and B to be measured, is used as a measuring system for measuring a transmittance variation due to such degradation caused by radiation. This measuring system is connected to a light source and an actinometer, for instance, with 11 and 15 allocated to the light-projecting and -receiving sides, so that the transmittance can be measured and so a transmittance variation due to the degradation caused by radiation can constantly be measured. Thus, the desired absorptiometric, fluorophotometric and other measurements can precisely be effected while the measurements of the fluids A and B are corrected on the basis of such measured transmittance variation.

As described above, a plurality of measurements can simultaneously be effected by varying the length, number, etc., of the leading ends, depending on many purposes. While the embodiments of the invention have been explained on the premise that optical fiber bundles are used as optical waveguides for guiding light to the leading ends 11 to 18 and guiding the received light to the photometric equipment 5, it is understood that each optical fiber bundle may be formed of a single optical fiber. Also, while the embodiments of the invention have been explained on condition that the reflecting prisms 7 are used to convert the light leaving the leading ends of optical fibers or optical fiber bundles into light at right angles with the axes thereof, and to turn the light incident on the optical fibers or optical fiber bundles at right angles in the axial direction thereof, it is understood that the optical fibers or optical fiber bundles may be bent 90°. Moreover, while the embodiments of the invention have been explained with the assumption that the positive lenses 6 are used to convert the light leaving optical fibers or optical fiber bundles into parallel light, and to converge the light beams propagating toward the leading ends of optical fibers or optical fiber bundles into the leading ends thereof, it is understood that concave mirrors or other optical elements may be used.

The multipurpose optical sensor of the invention being thus described with reference to some examples, it will be understood that the same is in no sense limited thereto, and so may be varied in many ways.

As can be seen from the foregoing, the invention enables a single multipurpose optical sensor to be simultaneously used for many purposes, e.g., absorptiometric, fluorophotometric, actinometric, and scattering-measuring purposes. The invention also enables a single optical sensor to be used for effecting a plurality of measurements of a plurality of samples while the influence index of radiation is compensated for.

The entirety of JP-7-45462 filed Mar. 6, 1995, from which priority under 35 USC 119 is claimed, is incorporated herein by reference.

What is claimed is:

1. A multipurpose optical sensor, comprising:

a plurality of optical fiber pairs; and an optical system for converting light guided through each of said optical fiber pairs and leaving leading ends of one optical fiber of each of said optical fiber pairs into a substantially parallel light beam in a direction at right angles with an axis thereof, and converging said substantially parallel light beam incident on said axis from a direction at right angles therewith and guiding the thus converged light beam from said leading ends into the other optical fiber of each of said optical fiber pairs in the form of guide light, said optical fiber pairs being concentrically located in the vicinity of said leading ends, each of said optical fiber pairs having a pair of opposing optical fibers, with the center of the concentric circle being positioned therebetween, being opposed to each other at an interval and disposed such that said substantially parallel light beam leaving one opposing optical fiber is incident on the other opposing optical fiber, and trailing ends of said optical fiber pairs being constructed such that said trailing ends separately receive or give out light, wherein a first pair of said plurality of optical fiber pairs measures a first type of measurement and a second pair of said plurality of optical fiber pairs measures a second type of measurement different from the first type of measurement.

2. The multipurpose optical sensor according to claim 1, wherein said optical systems are each constructed from a positive lens and at least one of a reflecting mirror and a prism.

3. The multipurpose optical sensor according to claim 1, wherein said optical system is constructed from a 90°-bent leading end portion of said optical fiber and a positive lens.

4. The multipurpose optical sensor according to claim 1, wherein when said pairs of said opposing optical fibers lie on axially identical positions.

5. The multipurpose optical sensor according to claim 1, wherein axial positions of said optical system located at the leading ends of different pairs of said plurality of optical fiber pairs are different.

6. The multipurpose optical sensor according to claim 1, wherein the leading ends of optical fibers of said optical fiber pairs are positioned at regular intervals on said concentric circle.

7. A multipurpose optical sensor according to claim 1, wherein optical fibers of said optical fiber pairs include optical fiber bundles.

8. An optical sensor, comprising:
   a cable with a leading end; and
   an optical system disposed at said leading end of said cable, said optical system including:
      a plurality of optical fiber pairs disposed within said cable and concentrically extending from said leading end of said cable, a first optical fiber of a first pair of said plurality of optical fiber pairs being positioned opposite a second optical fiber of the first pair;
      a first optical device disposed at an end of the first optical fiber to direct a light beam emanating from the first optical fiber perpendicularly across an axis of said cable; and
      a second optical device disposed at an end of the second optical fiber to receive the light beam directed from the first optical fiber and to transfer the light beam into the second optical fiber,
   wherein the first pair of said plurality of optical fiber pairs measures a first type of measurement and a second pair of said plurality of optical fiber pairs measures a second type of measurement different from the first type of measurement.

9. An optical sensor according to claim 8, wherein each pair of said plurality of optical fiber pairs provide measurements in different directions.

10. An optical sensor according to claim 8, wherein said plurality of optical fiber pairs measure at least two of absorptiometric, fluorophotometric, actinometric, and scattering measurements.

11. An optical sensor according to claim 8,
   wherein the first pair of said plurality of optical fiber pairs measures a transmittance variation resulting from radiation; and
   wherein the second pair of said plurality of optical fiber pairs measure at least one of absorptiometric, fluorophotometric, actinometric, and scattering measurements.

12. An optical sensor according to claim 8, wherein each pair of said plurality of optical fiber pairs extends from said leading end of said cable at different lengths.

13. An optical sensor according to claim 8, wherein each pair of said plurality of optical fiber pairs extends from said leading end of said cable at different lengths for measurements in different levels.

14. An optical sensor according to claim 8, wherein each optical fiber of each pair of said plurality of optical fiber pairs is an optical fiber bundle.

15. An optical sensor, comprising:
   a cable with a leading end; and
   an optical system disposed at said leading end of said cable, said optical system including:
      a plurality of optical fiber pairs disposed within said cable and concentrically extending from said leading end of said cable, a first optical fiber of a first pair of said plurality of optical fiber pairs being positioned opposite a second optical fiber of the first pair;
      a first optical device disposed at an end of the first optical fiber to direct a light beam emanating from the first optical fiber perpendicularly across an axis of said cable; and
      a second optical device disposed at an end of the second optical fiber to receive the light beam directed from the first optical fiber and to transfer the light beam into the second optical fiber,
   wherein said cable includes a trailing end, and
   wherein said plurality of optical fiber pairs include:
      a first optical fiber pair having corresponding ends at said trailing end of said cable being connected to an absorptiometer;
      a second optical fiber pair having corresponding ends at said trailing end of said cable being connected to a fluorophotometer; and
      a third optical fiber pair having corresponding ends at said trailing end of said cable being connected to an actinomer.

* * * * *